United States Patent [19]
Shima

[11] Patent Number: 5,534,029
[45] Date of Patent: Jul. 9, 1996

[54] ARTICULATED VERTEBRAL BODY SPACER

[75] Inventor: Toshio Shima, Kanagawa, Japan

[73] Assignee: Yumiko Shima, Kanagawa, Japan

[21] Appl. No.: 160,487

[22] Filed: Dec. 1, 1993

[30] Foreign Application Priority Data

Dec. 14, 1992 [JP] Japan .................................. 4-352925

[51] Int. Cl.$^6$ ................................ A61F 2/44; A61B 17/56
[52] U.S. Cl. ................................................ 623/17; 606/61
[58] Field of Search ............................ 623/17–18, 2030; 606/60, 61, 62, 63, 64

[56] References Cited

U.S. PATENT DOCUMENTS

| | | | |
|---|---|---|---|
| 4,759,766 | 7/1988 | Buettner-Jamz et al. | 623/17 |
| 5,071,437 | 12/1991 | Steffee | 623/17 |
| 5,258,031 | 11/1993 | Salib et al. | 623/17 |
| 5,360,430 | 11/1994 | Lin | 606/61 |

FOREIGN PATENT DOCUMENTS

| | | | |
|---|---|---|---|
| 3023353 | 4/1981 | Germany | 623/17 |
| 4-99570 | 3/1992 | Japan . | |

*Primary Examiner*—Debra S. Brittingham
*Attorney, Agent, or Firm*—Blakely, Sokoloff, Taylor & Zafman

[57] ABSTRACT

An articulated vertebral body spacer is constituted by a pair of upper and lower joint pieces to be inserted between vertebras. The lower joint piece includes a convex portion formed on a central portion of its upper surface and having a convex sliding contact surface, and a stopper surface surrounding the convex portion. The upper joint piece includes a concave portion formed on a central portion of its lower surface and having a concave sliding contact surface which is sliding contact with the convex sliding contact surface, and an abutment surface which surrounds the concave portion and abuts against the stopper surface. A cavity for allowing the upper joint piece to pivot in accordance with forward/backward and bending motions of vertebral bodies to respective levels is formed between the abutment surface and the stopper surface.

4 Claims, 5 Drawing Sheets

FIG.12

ARTICULATED VERTEBRAL BODY SPACER

BACKGROUND OF THE INVENTION

The present invention relates to an articulated vertebral body spacer suitably inserted between vertebras such as cervical vertebras, thoracic vertebras, and lumbar vertebras, an intervertebral cavity measuring device, and a vertebral body spacer model.

In the case of a hernia of an intervertebral disk or a rupture of a vertebral body due to a malignant tumor, the intervertebral disk or the vertebral body is surgically removed. If the space left after the removal is narrow, no special treatment is performed. If the space is wide, a patient's own peripheral bone, an artificial vertebral body, or the like is inserted between the vertebras. If an autologous bone is used, it is free from a rejection symptom. An artificial vertebral body used nowadays is free from a rejection symptom and has a strong affinity for a bone.

The spine has a movable structure. If, therefore, a rigid intervertebral spacer is inserted between movable portions of the spine, the vertebral bodies and the spacer may be physically separated from each other every time the spine moves, even though the spacer has a strong affinity for a bone. For this reason, the present applicant has proposed articulated vertebral body spacer (Japanese Patent Application No. 2-217062). This spacer is constituted by a pair of upper and lower members respectively having concave and convex joint surfaces on their opposite surfaces. With this structure, a uniform pressure is applied to the contact surfaces between the vertebral bodies and the spacer so as to prevent separation or disengagement of the spacer.

The following problem, however, is posed in the articulated vertebral body spacer previously proposed by the present applicant, which spacer is constituted by the pair of upper and lower members respectively having concave and convex sliding contact surfaces on their opposite surfaces. Since the entire opposite surfaces of the upper and lower members are sliding contact surfaces, the spacer cannot restrict the inclination of the vertebral bodies. If, therefore, the vertebral bodies are inclined greatly, the joint may be separated or disengaged from the vertebral bodies. When a plurality of vertebral bodies are replaced, by increasing the number of joints to two or three, physiological curves can be formed in vertebral bodies. With these curves, it is expected that the disengagement of an artificial vertebral body join (articulated vertebral body spacer) can be prevented.

In a surgical operation on the cervical vertebras, an intervertebral disk is removed. Measurement of the depth and thickness of this intervertebral disk ablation cavity (intervertebral cavity) is indispensable for the insertion of a vertebral body spacer. A conventional depth gage for measuring the depth of an intervertebral cavity is a rod-like member and is insufficient for measurement of depth and thickness. If a vertebral body spacer model is formed, and an intervertebral cavity is formed to fit thereto, it is expected that insertion of an articulated vertebral body spacer can be easily and reliably performed.

SUMMARY OF THE INVENTION

It is a principal object of the present invention to provide an articulated vertebral body spacer which fills an ablation cavity between vertebras, maintains the strength of each vertebral body, ensures a moving function between the vertebras, eliminates a nonphysiological burden on the upper and lower vertebras, and can reliably prevent separation and disengagement.

It is another object of the present invention to provide an intervertebral cavity measuring device which can measure the depth or thickness of an intervertebral cavity.

It is still another object of the present invention to provide a vertebral body spacer model which allows the formation of an intervertebral cavity matching an articulated vertebral body spacer.

In order to achieve the above objects, according to an aspect of the present invention, there is provided an articulated vertebral body spacer comprising a pair of upper and lower joint pieces to be inserted between vertebras, the lower joint piece including a convex portion formed on a central portion of an upper surface thereof and having a convex sliding contact surface, and a stopper surface surrounding the convex portion, and the upper joint piece including a concave portion formed on a central portion of a lower surface thereof and having a concave sliding contact surface which is sliding contact with the convex sliding contact surface, and an abutment surface which surrounds the concave portion and abuts against the stopper surface, wherein a cavity for allowing the upper joint piece to pivot in accordance with forward/backward and bending motions of vertebral bodies to respective levels is formed between the abutment surface and the stopper surface.

According to another aspect of the present invention, there is provided an articulated vertebral body spacer comprising upper and lower joint pieces to be inserted between vertebras, and at least one intermediate vertebral body interposed between the upper and lower joint pieces, said spacer defining front and rear sides, the lower joint piece including a convex portion formed on a central portion of an upper surface thereof and having a convex sliding contact surface, and a stopper surface surrounding the convex portion, the upper joint piece including a concave portion formed on a central portion of a lower surface thereof and having a concave sliding contact surface, and an abutment surface which surrounds the concave portion and abuts against the stopper surface, and the intermediate vertebral body including a concave portion formed on a central portion of a lower surface thereof and having a concave sliding contact surface which is in sliding contact with the convex sliding contact surface of the lower joint piece, an abutment surface surrounding the concave portion and abutting against the stopper surface of the lower joint piece, a convex portion formed on a central portion of an upper surface of the intermediate vertebral body and having a convex surface which is in sliding contact with the concave sliding contact surface of the upper joint piece, and a stopper surface surrounding the convex portion and abutting against the abutment surface of the upper joint piece, wherein the stopper surface of the lower joint piece and the abutment surface of the intermediate vertebral body and between the abutment surface of the upper joint piece and the stopper surface of the intermediate vertebral body define gaps such that said gaps formed in said front side are larger than said gaps formed in said rear side.

According to still another embodiment of the present invention, there is provided an intervertebral cavity measuring device comprising an elongated rod-like member and a plate-like portion which is mounted on a distal end of the rod-like member and measures a size of an intervertebral cavity.

According to still another aspect of the present invention, there is provided a vertebral body spacer model comprising

DESCRIPTION OF THE PREFERRED EMBODIMENTS

The present invention will be described in detail below with reference to the embodiments shown in the accompanying drawings.

Figure 1:
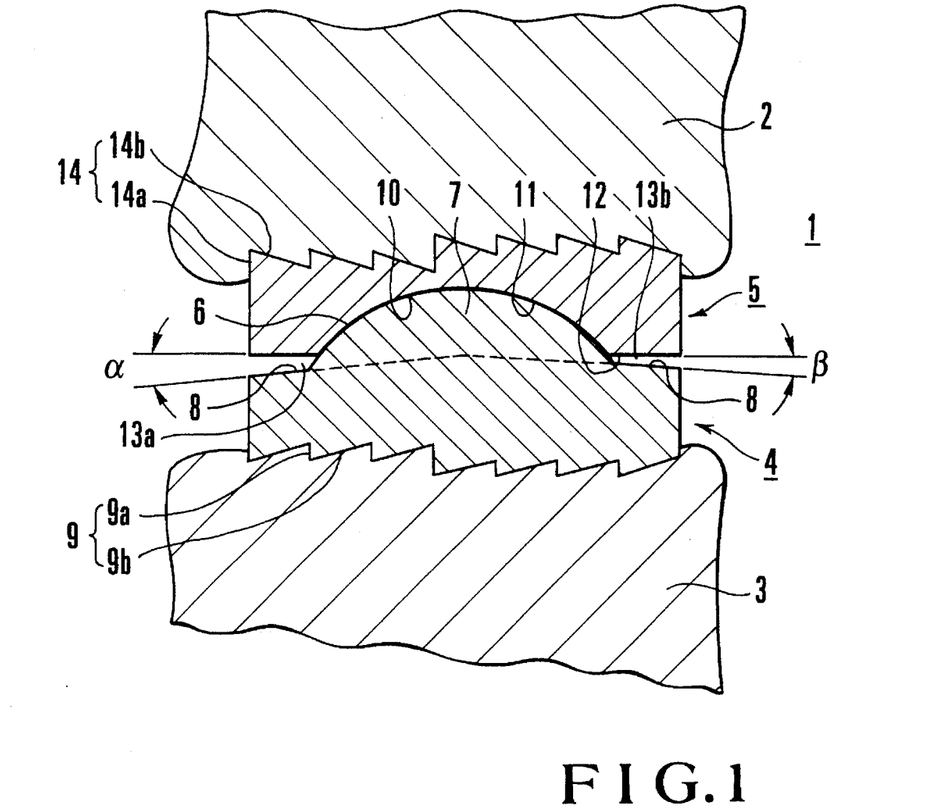
FIG. 1 is a sectional view showing an embodiment of an articulated vertebral body spacer according to the present invention.
Figure 2:
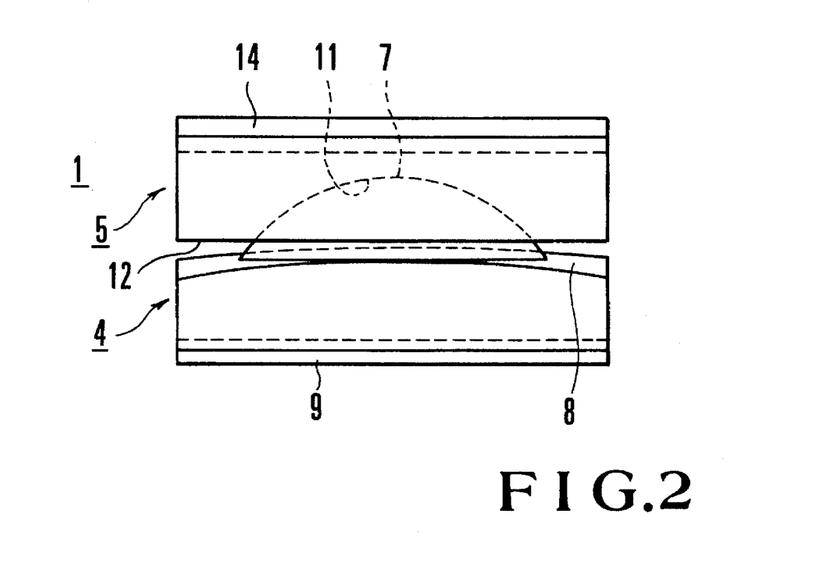
FIG. 2 is a front view showing a joint in FIG. 1.
Figure 3:
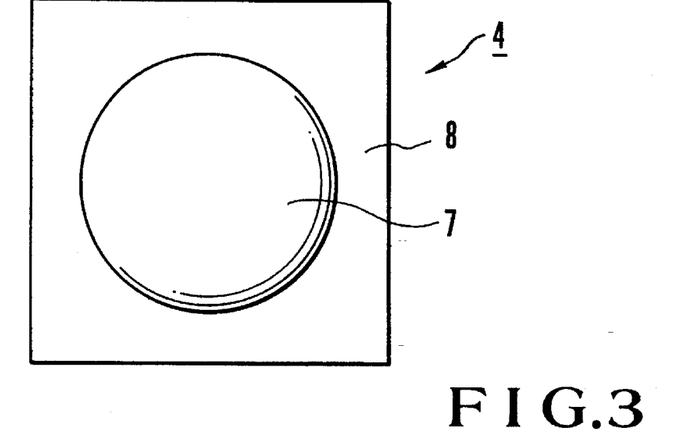
FIG. 3 is a plan view of a lower joint piece in FIG. 1.

FIGS. 1 to 3 show an embodiment of an articulated vertebral body spacer of the present invention. Referring to FIGS. 1 to 3, an articulated vertebral body spacer 1 is constituted by a pair of upper and lower joint pieces 4 and 5 respectively having sliding contact surfaces which are in tight contact with each other. The joint pieces 4 and 5 are inserted between cervical vertebras 2 and 3. The joint pieces 4 and 5 respectively have shapes suitably fixed to the cervical vertebras 2 and 3. In this embodiment, the cervical vertebras 2 and 3 are the fifth and sixth cervical vertebras, respectively.

The lower joint piece 4 is constituted by a rectangular plate-like member having an outer shape of a size (e.g., 8 mm×14 mm×14 mm) almost equal to that of the upper surface shape of the cervical vertebra 3 on the lower side. A convex portion 7 having a spherical sliding contact surface 6 with a proper curvature radius is integrally formed on a central portion of the upper surface of the lower joint piece 4. In addition, an upper peripheral portion surrounding the convex portion 7 constitutes a stopper surface 8. The front and rear sides of the stopper surface 8 are formed into inclined surfaces inclined at different angles α and β. A material having a small friction coefficient may be used for the sliding contact surface 6 of the convex portion 7, or a special treatment or a cap may be provided for the surface to prevent wear. The height of the lower joint piece 4 is set in accordance with the height of a vertebral body ablation portion. A large number of saw-tooth projections 9 integrally extend from the lower surface of the lower joint piece 4. The projections 9 are buried in the upper surface of the cervical vertebra 3 to prevent the forward/backward movement and disengagement of the lower joint piece 4 with respect to the cervical vertebra 3. Each projection 9 is constituted by a vertical surface 9a and an inclined surface 9b. The vertical surface 9a is located toward the front at the time of mounting the articulated vertebral body spacer 1. The inclined surface 9b extends backward from the vertical surface 9a to be inclined at a predetermined angle.

The upper joint piece 5 has a plate-like shape having almost the same outer shape as that of the lower joint piece 4. A concave portion 11 having a concave sliding contact surface 10 with substantially the same curvature radius as that of the convex sliding contact surface 6 is formed on a central portion of the lower surface of the upper joint piece 5. A lower peripheral portion surrounding the concave portion 11 is formed into an abutment surface 12 which abuts against the stopper surface 8. The abutment surface 12 is formed to have a substantially horizontal flat surface. In a normal state, the abutment surface 12 opposes the stopper surface 8 of the lower joint piece 4, and proper gaps 13a and 13b are formed between these surfaces. A large number of saw-tooth projections 14 are integrally formed on the upper surface of the upper joint piece 5. The projections 14 are buried in the lower surface of the cervical vertebra 2 to fix the upper joint piece 5 thereto, thereby preventing the forward/backward movement and disengagement of the upper joint piece 5. Similar to the projection 9 described above, each of the projections 14 is constituted by a vertical surface 14a and an inclined surface 14b. The vertical surface 14a is located toward the front at the time of mounting the articulated vertebral body spacer 1. The inclined surface 14b extends backward from the vertical surface 14a to be inclined at a predetermined angle.

The surfaces, of the upper and lower joint pieces 5 and 4, which are fixed to the cervical vertebras 2 and 3 may have any structures as long as they can prevent movement and disengagement. For example, a spindle type structure or a granular type structure.

Note that, for example, the values of the forward and backward inclination angles α and β of the stopper surface 8 are set to satisfy α+β=10° to 20° for the cervical vertebras; α+β=4° to 12° for the thoracic vertebras; and α+β=12° to 17° for the lumbar vertebras, while the value of α is set to be larger than the value of β.

As a material for the upper and lower joint pieces 5 and 4, a physically and chemically stable inorganic material, e.g., an alumina ceramic material, a zirconia ceramic material, or a calcium phosphate ceramic material, is used. Of these materials, especially an alumina ceramic material exhibits high stability in a living body and has strong affinity for living tissue.

When the articulated vertebral body spacer 1 having the above-described arrangement is to be inserted between the cervical vertebras 2 and 3, stepped recess portions are formed on the opposite surfaces of the cervical vertebras 2 and 3 in correspondence with the projections 9 and 14, and a model (to be described later) of an artificial vertebral body joint to be inserted is formed in advance. An insertion cavity having a size matching the model is formed. Thereafter, the articulated vertebral body spacer 1 is inserted between the cervical vertebras 2 and 3, and the projections 9 and 14 of the upper and lower joint pieces 5 and 4 are buried or fitted in the recess portions of the cervical vertebras 2 and 3, respectively. In addition, if the upper and lower joint pieces are respectively fixed to the vertebral bodies with screws or front beak-like protruding pieces, the stability can be improved. When the articulated vertebral body spacer 1 is inserted between the cervical vertebras 2 and 3 in this manner, the upper and lower joint pieces 5 and 4 are respectively assimilated to the cervical vertebras 2 and 3. With the relative sliding motions of the sliding contact surfaces 6 and 10, the forward/backward motions and transverse/longitudinal joint motions of the cervical vertebra intervertebral cavity are allowed.

Figure 4:
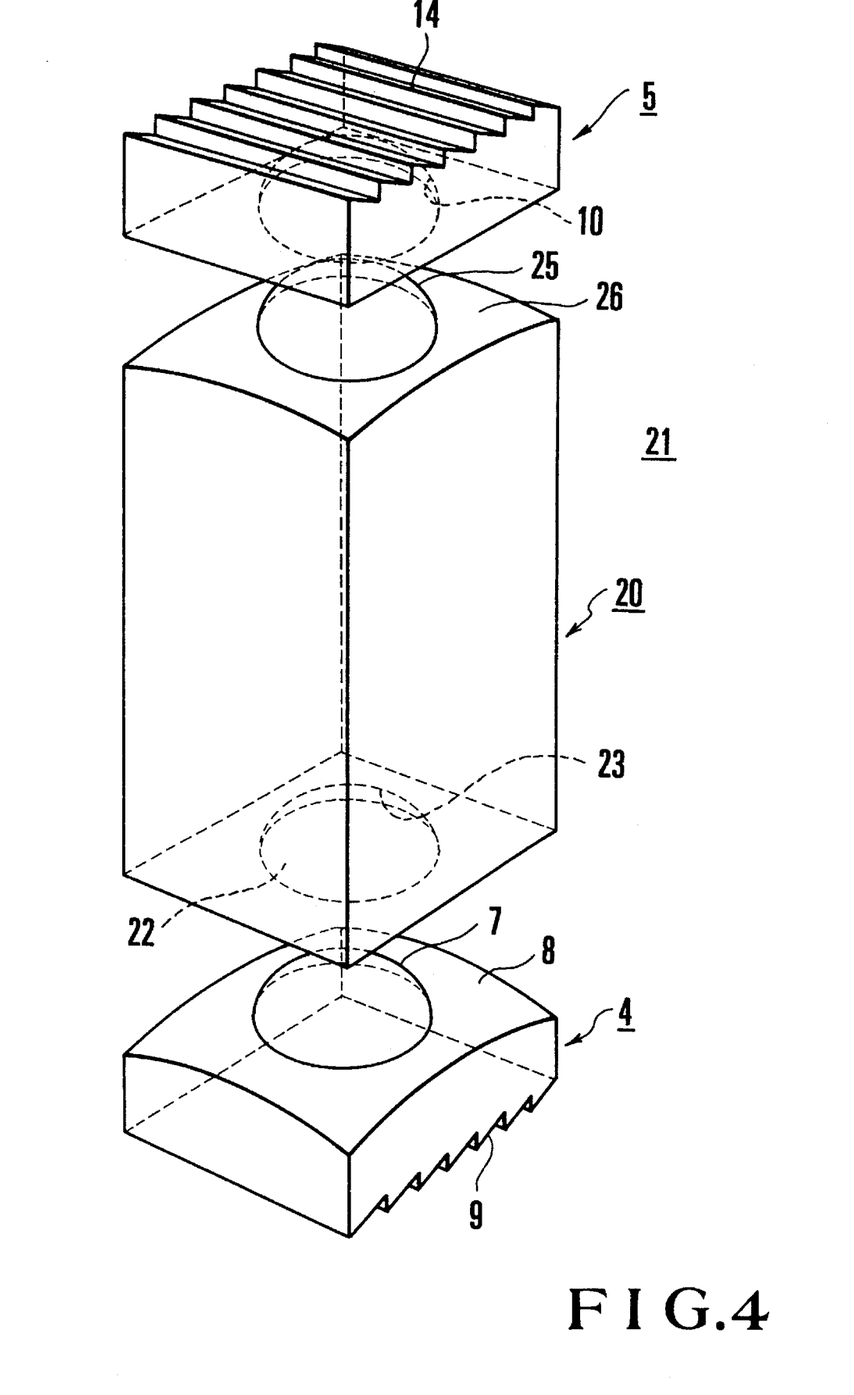
FIG. 4 is an exploded perspective view showing another embodiment of the present invention.
Figure 5:
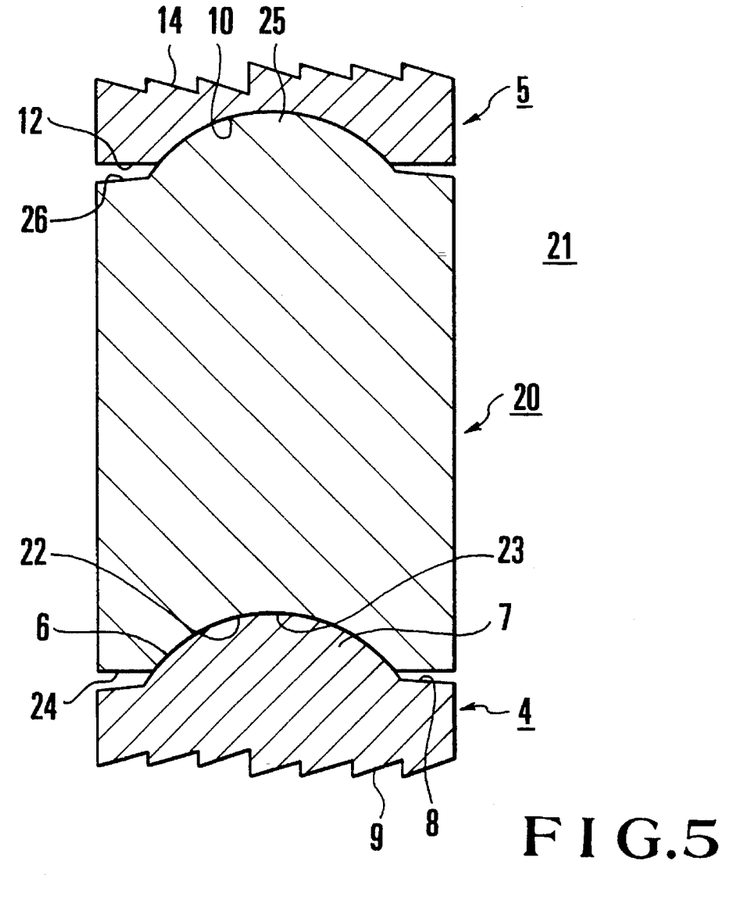
FIG. 5 is a longitudinal sectional view of FIG. 4.

FIGS. 4 and 5 show another embodiment of the present invention. In this embodiment, an articulated vertebral body spacer 21 is constituted by three members, i.e., a lower joint piece 4, an intermediate vertebral body 20, and an upper joint piece 5, and is inserted between upper and lower vertebras after the vertebral body located therebetween is removed (for example, between the fifth and seventh cervical vertebral bodies after the sixth cervical vertebral body is removed). The intermediate vertebral body 20 is formed of a relatively high block-like member. A concave portion 23 is formed on a central portion of the lower surface of the intermediate vertebral body 20. The concave portion 23 has a concave sliding contact surface 22 which is in sliding contact with a convex sliding contact surface 6 of the lower joint piece 4. A lower peripheral portion surrounding the concave portion 23 is formed into an abutment surface 24 which opposes and abuts against a stopper surface 8 of the lower joint piece 4. A convex portion 25 which is in sliding contact with a concave sliding contact surface 10 of the upper joint piece 5 is integrally formed on a central portion of the upper surface of the intermediate vertebral body 20. An upper peripheral portion surrounding the convex portion 25 is formed into a stopper surface 26 which opposes and abuts against an abutment surface 12 of the upper joint piece 5. Other arrangements are the same as those of the first embodiment described above.

By variously changing the height of the intermediate vertebral body 20, the articulated vertebral body spacer 21 having the above-described arrangement can be suitably applied to a case wherein the vertebral body ablation, i.e., the intervertebral ablation, is large.

Each embodiment described above is associated with the case wherein the articulated vertebral body spacer is inserted between the cervical vertebras. The present invention is not specified by the embodiments in any way. It is apparent that by changing the heights, depths, widths, and angles of the respective components of the articulated vertebral body spacers of the embodiments, the spacers can be applied to the thoracic vertebras and lumbar vertebras.

The present invention is not limited to the above-described embodiments, and various changes and modifications can be made. For example, two or more intermediate vertebral bodies 20 may be used as needed. In addition, a small projection may be formed on the vertex of one of spherical sliding contact surfaces which are in sliding contact with each other, while a recess portion in which the small projection can be fitted is formed in the other sliding contact surface. Furthermore, surfaces, of the intermediate vertebral body 20, which are in contact with a bone may be roughened, or a wedge may be driven between the intermediate vertebral body 20 and a bone, thereby more reliably preventing separation and disengagement of the articulated vertebral body spacer when the vertebral body bends and extends.

Figure 6:
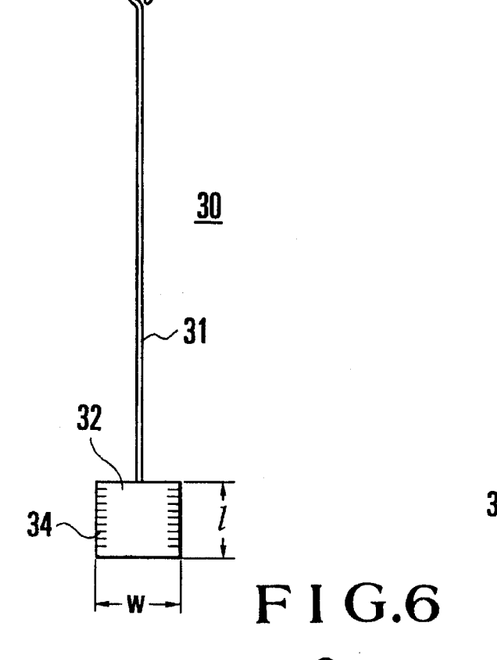
FIG. 6 is a front view showing an embodiment of an intervertebral cavity measuring device for measuring the depth of an intervertebral cavity.
Figure 7:
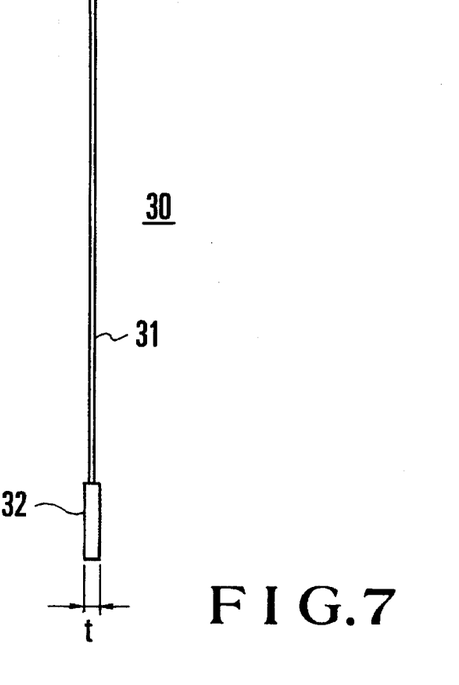
FIG. 7 is a side view of FIG. 6.
Figure 8:
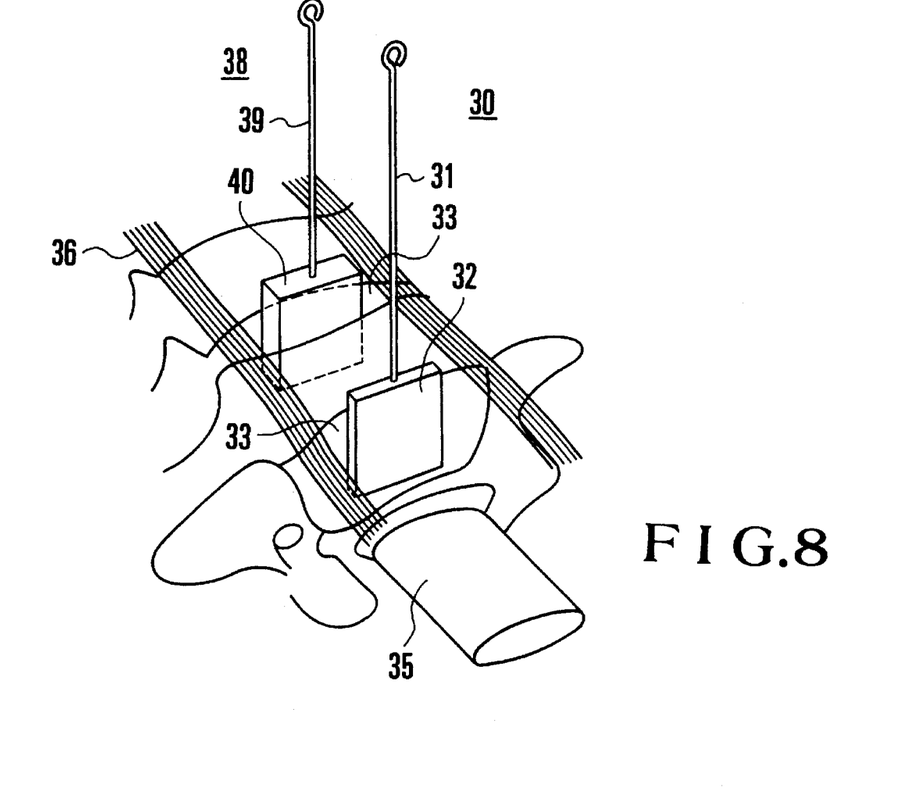
FIG. 8 is a perspective view showing a state of measurement.

FIGS. 6 to 8 show an embodiment of an intervertebral cavity measuring device for measuring the depth of an intervertebral cavity. Referring to FIGS. 6 to 8, an intervertebral cavity measuring device 30 is constituted by an elongated rod-like member 31 and a plate-like member 32 having a predetermined thickness. The plate-like member 32 is mounted on the distal end of the rod-like member 31 and is inserted into an intervertebral cavity 33. Scale marks 34 for measuring the depth of the intervertebral cavity 33 are graduated on two side edges of the plate-like member 32. As the rod-like member 31, for example, a stainless steel wire having a diameter of about 1 mm is used. The plate-like member 32 is made of a material which can withstand high-pressure steam sterilization, such as stainless steel, a ceramic material, or a synthetic resin. The plate-like member 32 has a thickness t=2 mm, a width w=14 mm, and a length l=13 mm. Each scale mark 34 is graduated in millimeters.

In measuring the depth of the intervertebral cavity 33 after an intervertebral disk is removed, a plurality of intervertebral cavity measuring devices 30 having plate-like members 32 of different lengths l are prepared. For example, four types of intervertebral cavity measuring devices 30 respectively having lengths l of 13 mm, 14 mm, 15 mm, and 16 mm are prepared. By selecting a proper intervertebral cavity measuring device 30 corresponding to the depth of the intervertebral cavity 33, and inserting its plate-like member in the intervertebral cavity 33, a proper depth can be known, thus obtaining an actual feeling at the time of inserting an intervertebral space in a surgical operation.

Note that by changing the width w, length l, and thickness t of the plate-like member 32, measuring devices for the thoracic vertebras and lumbar vertebras can be formed. Reference numeral 35 denote a spine; and 36, muscles.

Figure 9:
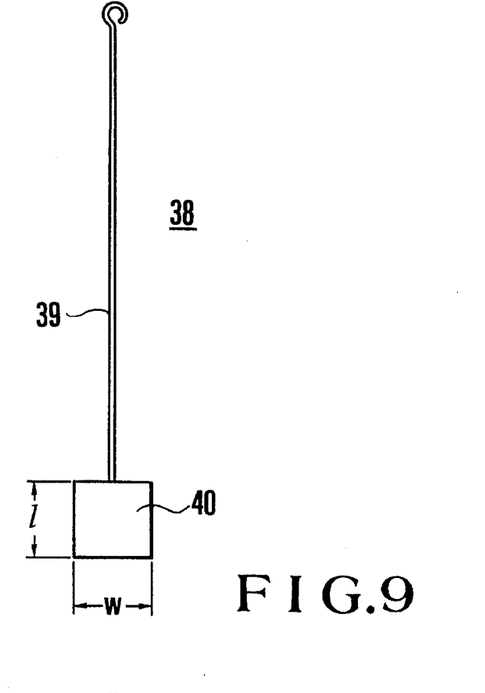
FIG. 9 is a front view showing an embodiment of an intervertebral cavity measuring device for measuring the thickness of an intervertebral cavity.
Figure 10:
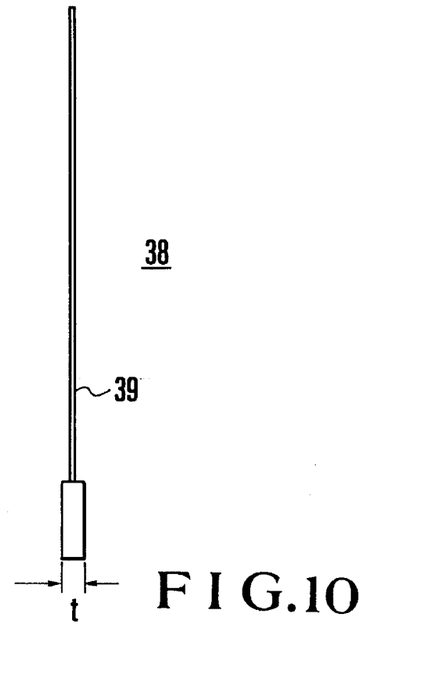
FIG. 10 is a side view of FIG. 9.

FIGS. 9 and 10 show an embodiment of an intervertebral cavity measuring device for measuring the thickness of an intervertebral cavity. Referring to FIGS. 9 and 10, an intervertebral cavity measuring device 38 is constituted by an elongated rod-like member 39 and a plate-like member 40 having a predetermined thickness. The plate-like member 40 is mounted on the distal end of the rod-like member 39 and is inserted into an intervertebral cavity. As the rod-like member 39, a stainless steel wire having a diameter of about 1 mm is used. The plate-like member 40 is made of a material which can withstand high-pressure steam sterilization, such as stainless steel, a ceramic material, or a synthetic resin. The plate-like member 40 has a width w=14 mm, a length l=14 mm, and a thickness t=4 mm.

In measuring the thickness of an intervertebral cavity after an intervertebral disk is removed, a plurality of intervertebral cavity measuring devices 38 having plate-like members 40 of different thicknesses t are prepared. For example, four types of intervertebral cavity measuring devices 38 respectively having thicknesses t of 4 mm, 6 mm, 8 mm, and 10 mm are prepared. Upper and lower cervical vertebras are pulled to expand the intervertebral cavity, and a plate-like portion having a thickness almost equal to the thickness of the intervertebral cavity in this state is selected, thus performing measurement.

Note that by changing the width w, length l, and thickness t of the plate-like member 32, measuring devices for the thoracic vertebras and lumbar vertebras can be formed.

Figure 11:
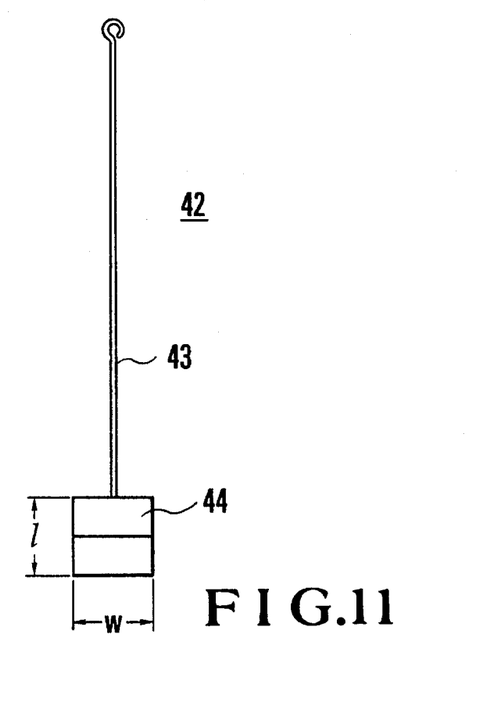
FIG. 11 is a front view showing an embodiment of a vertebral body spacer model.
Figure 12:
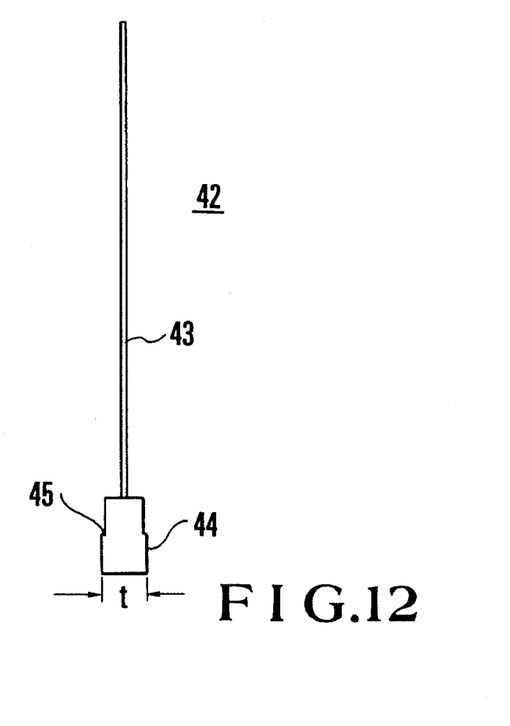
FIG. 12 is a side view of FIG. 11.

FIGS. 11 and 12 show an embodiment of a vertebral body spacer model. Referring to FIGS. 11 and 12, a vertebral body spacer model 42 is constituted by a rod-like member 43 consisting of stainless steel and a model main body 44 composed of a cube having a predetermined size. The model main body 44 is mounted on the distal end of the vertebral body spacer model 42 and is inserted into an intervertebral cavity. As the vertebral body spacer model 42, for example, a stainless steel wire having a diameter of about 1 mm is used. The model main body 44 is made of a material which can withstand high-pressure sterilization, such as stainless steel, a ceramic material, or a synthetic resin. The model main body 44 has a width w=14 mm, a length (depth) l=14 mm, and a thickness (height) t=8 mm. A step 45 is formed on a vertically central portion of the model main body 44, which is brought into contact with a cervical vertebra when the model main body 44 is inserted into a long intervertebral cavity. The step 45 has a thickness of about 0.5 mm. With the step 45, the front end side portion of the model main body 44 is thinner than its rear end side portion. A plurality of vertebral body spacer models having model main bodies 44 of different thicknesses t are prepared. For example, 10 types of vertebral body spacer models 42 having different thicknesses t ranging from 25 mm to 34 mm in unitary increments are prepared.

In inserting an articulated vertebral body spacer, upper and lower cervical vertebras are pulled to expand the intervertebral cavity by a predetermined amount. In this state, a model main body 44 having a size substantially equal to that of the intervertebral cavity is selected, and a cervical vertebra is cut with a drill to form an intervertebral cavity matching this model main body 44. In addition, an articulated vertebral body spacer having the same size as that of the vertebral body spacer model 42 is manufactured in advance and is inserted/fixed in the intervertebral cavity. If an intervertebral cavity matching the size of the vertebral body spacer model 42 is formed in this manner, the articulated vertebral body spacer can be easily and reliably inserted.

As has been described above, the articulated vertebral body spacer according to the present invention is constituted by a pair of upper and lower joint pieces which are inserted between vertebras. The upper and lower joint pieces respectively having concave and convex sliding contact surfaces which are in tight contact with each other and slide on each other, and stopper and abutment surfaces which surround the sliding contact surfaces, oppose each other, and abut against each other. With this arrangement, joint motions of an intervertebral cavity can be ensured to reduce the nonphysiological burden on other normal vertebras. In addition, since the inclination of each joint piece in intervertebral bending/extending motions is restricted by the stopper and abutment surfaces, separation, disengagement, and the like of each joint piece can be reliably prevented.

In addition, since the present invention is constituted by upper and lower joint pieces and at least one intermediate vertebral body interposed therebetween, the use of a plurality of intermediate joint pieces provides better effects in case of a larger vertebral body ablation.

Furthermore, according to the intervertebral cavity measuring devices of the present invention, the depth and thickness of an intervertebral cavity can be easily and reliably measured.

Moreover, when an intervertebral cavity is formed by using the vertebral body spacer model of the present invention, an articulated vertebral body spacer can be easily and reliably inserted.

What is claimed is:

1. An articulated vertebral body spacer comprising:

upper and lower joint pieces to be inserted between vertebras, and at least one intermediate vertebral body interposed between said upper and lower joint pieces, said spacer defining first and rear sides, said lower joint piece including a convex portion formed on a central portion of an upper surface thereof and having a convex sliding contact surface, a stopper surface surrounding the convex portion, and a plurality of projections provided on a lower surface of the lower joint piece, said upper joint piece including a concave portion formed on a central portion of a lower surface thereof and having a concave sliding contact surface, an abutment surface which surrounds the concave portion, and a plurality of projections provided on an upper surface of the upper joint piece, and said intermediate vertebral body including a concave portion formed on a central portion of a lower surface thereof and having a concave sliding contact surface which is in sliding contact with the convex sliding contact surface of said lower joint piece, an abutment surface surrounding the concave portion and abutting against the stopper surface of said lower joint piece, a convex portion formed on a central portion of an upper surface of said intermediate vertebral body and having a convex surface which is in sliding contact with the concave sliding contact surface of said upper joint piece, and a stopper surface surrounding the convex portion and abutting against the abutment surface of said upper joint piece, wherein the stopper surface of said lower joint piece and the abutment surface of said intermediate vertebral body and between the abutment surface of said upper joint piece and the stopper surface of said intermediate vertebral body define gaps such that said gaps formed in said front side are larger than said gaps formed in said rear side.

2. A spacer according to claim 1, wherein movement preventing structures are formed on the lower surface of said lower joint piece and the upper surface of said upper joint piece.

3. A spacer according to claim 1, wherein the stopper surface is formed such that a front surface side portion is lower than a central side portion.

4. A spacer according to claim 1, wherein each of the gaps is determined such that a front side gap is larger than a rear side gap in an upright posture.

\* \* \* \* \*

UNITED STATES PATENT AND TRADEMARK OFFICE
CERTIFICATE OF CORRECTION

PATENT NO. : 5,534,029
DATED : July 9, 1996
INVENTOR(S) : Shima

It is certified that error appears in the above-indentified patent and that said Letters Patent is hereby corrected as shown below:

In column 6 at lines 27,47,49, and 56, please delete " t " and insert -- t --.

In column 6 at lines 26 and 55, please delete " w " and insert -- w --.

In column 6 at line 43, please delete " 1 " and insert -- l --.

In column 6 at lines 26 and 55, please delete " 1 " and insert -- L --.

Signed and Sealed this

Twelfth Day of August, 1997

Attest:

BRUCE LEHMAN

Attesting Officer

Commissioner of Patents and Trademarks